United States Patent [19]

Nicks et al.

[11] Patent Number: 5,422,269
[45] Date of Patent: Jun. 6, 1995

[54] DECOMPOSITION OF ETHYLENICALLY UNSATURATED CARBOXYLIC ESTERS

[75] Inventors: Peter F. Nicks, Maidenhead; Mark A. Carber, Stockton on Tees; Julian M. Relton, Darlington, all of Great Britain

[73] Assignee: Imperial Chemical Industries plc, London, United Kingdom

[21] Appl. No.: 930,560

[22] PCT Filed: Mar. 28, 1991

[86] PCT No.: PCT/GB91/00483

§ 371 Date: Nov. 30, 1992

§ 102(e) Date: Nov. 30, 1992

[87] PCT Pub. No.: WO91/15520

PCT Pub. Date: Oct. 17, 1991

[30] Foreign Application Priority Data

Mar. 30, 1990 [GB] United Kingdom ............... 9007140

[51] Int. Cl.$^6$ ............................................ C08F 6/16
[52] U.S. Cl. .......................... 435/262.5; 210/632; 528/491
[58] Field of Search ................... 524/21, 26, 819; 525/54.1, 54.11; 528/491; 435/262, 262.5; 210/632

[56] References Cited

U.S. PATENT DOCUMENTS

| | | | |
|---|---|---|---|
| 3,897,308 | 7/1975 | Li et al. | 435/262 |
| 4,133,752 | 1/1979 | Kurane et al. | 435/262 |
| 4,623,465 | 11/1986 | Klibanov | 210/632 |
| 4,766,173 | 8/1988 | Bailey et al. | 524/819 |
| 5,110,740 | 5/1992 | Pokora et al. | 435/262 |
| 5,145,890 | 9/1992 | Frederick et al. | 435/262 |

FOREIGN PATENT DOCUMENTS 272025  6/1988  European Pat. Off. .
1272584  5/1972  United Kingdom .

OTHER PUBLICATIONS

R. Tor et al., "Enzymatically catalysed transesterifications of acryl and methacryl monomeric esters", Enzyme Microb. Technol. vol. 12, Apr. 1990, pp. 299–304.
Nakagawa, "Purification of Some Properties of Intercellular Esterase from Pseudomonas Fluoroscens".

Primary Examiner—Joseph L. Schofer
Assistant Examiner—Tom Weber
Attorney, Agent, or Firm—Cushman Darby & Cushman

[57] ABSTRACT

Residual levels of monomeric ethylenically unsaturated carboxylic acid esters such as alkyl acrylate and methacrylates, especially ethyl, butyl and "iso-hexyl" acrylates and methacrylates, in surfactant stabilised dispersions of polymers of the monomer(s) such as latices or products formulated from latices, are reduced by treatment with a hydrolytic enzyme, particularly a lipase or esterase. The treatment reduces and can obviate the perceived bad odour of the dispersions arising from the presence of the monomers.

6 Claims, 3 Drawing Sheets

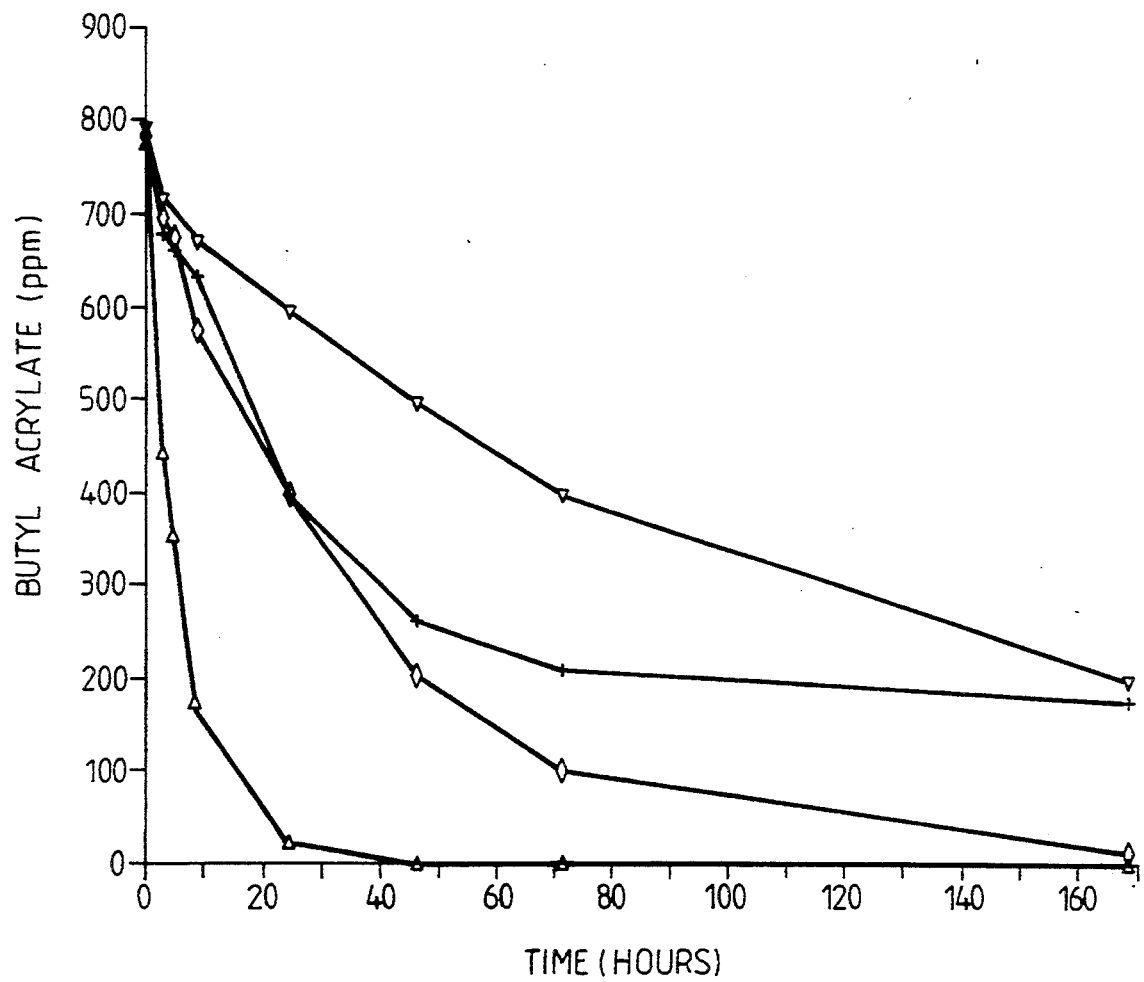

DECOMPOSITION OF ETHYLENICALLY UNSATURATED CARBOXYLIC ESTERS

This invention relates to a process for the decomposition of ethylenically unsaturated carboxylic esters, in particular acrylate and methacrylate esters. It also relates to latexes treated by the process.

Methyl, ethyl, butyl and higher acrylates and methacrylates are useful monomers which can be polymerised to form plastics especially thermoplastics materials having a wide range of uses. In particular these materials find extensive applications in coating compositions, e.g. paints, varnishes and stains and in wall covering materials. The utility of acrylate and methacrylate polymers is limited to some extent because they are generally contaminated with unreacted acrylate and methacrylate monomers which, particularly in the case of ethyl and butyl acrylates, can impart an unpleasant smell to the polymer. The unreacted monomer may be present in amounts up to 1000 or 2000 ppm in some polymers and is considered quite malodorous when present in amounts above 50 ppm. Contamination with unreacted monomer is particularly a problem when the polymer is used in paints and wall coverings when the smell is especially noticeable. This problem has for some considerable time concerned manufacturers of paints and wall coverings but, to date, no fully satisfactory solution has been found. Proposed methods for removing unreacted monomers from acrylate and methacrylate polymers have suggested using chemical treatments including those disclosed in U.S. Pat. No. 4,766,173 (treatment with cysteine and lysine), European Published Patent Application 0273651A (treatment with a scavenger monomer such as vinyl acetate) and German Offenlegenschrift 3635367.

We have now found that unreacted acrylate and methacrylate monomers can be removed from polymers by treatment with suitable enzymes.

Accordingly the present invention provides a method of removing residual amounts of an ethylenically unsaturated carboxylic acid ester monomer from a dispersion in a continuous liquid phase of particles of a polymer which contains residues derived from the ester monomer, which method comprises contacting the dispersion with a hydrolytic enzyme capable of decomposing the ester monomer in the presence of the stabilized dispersed polymer, under conditions suitable for the enzyme to decompose the ester.

Further according to the present invention we provide a latex comprising a polymerised ethylenically unsaturated carboxylic ester which contains at least 0.001% by weight (based on the weight of the latex) of a hydrolytic enzyme capable of decomposing the ester monomer.

BRIEF EXPLANATION OF THE DRAWINGS

In the accompanying Figures, FIGS. 1 to 3 are graphs showing the reduction of acrylate monomer levels occurring on treatment of polymer dispersions with enzymes according to the invention.

Figure 1:
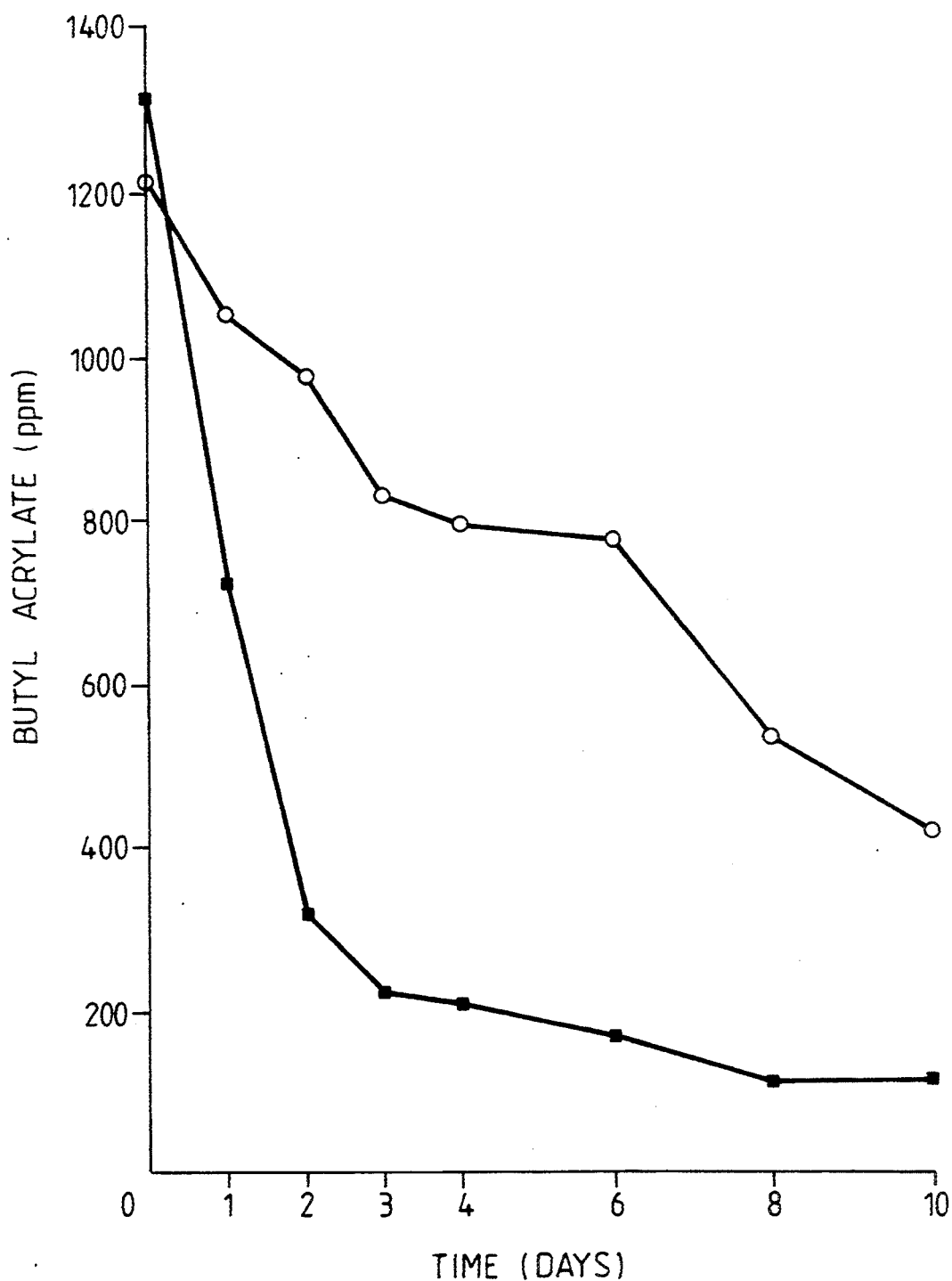

The process of the invention is especially suitable for the decomposition of unreacted acrylate and methacrylate monomers from acrylate and methacrylate polymers. Typically, the corresponding monomers are alkyl acrylate and/or methacrylate esters and usually the alkyl groups are $C_1$ to $C_{10}$ alkyl groups including, for example, ethyl, butyl and 'iso-octyl' (2-ethylhexyl) alkyl groups, together with pigments fillers and additives such as are commonly used in paint formulations. The process is also especially useful when the unreacted monomer is present in only trace amounts, say less than 2000 ppm. It can be used to treat polymers which are intended for any purpose but has particular advantages when used to treat polymers for use in wall coverings and coatings compositions e.g. paints, varnishes and stains. Treatment of the polymer with the enzyme can be carried out at any stage during its production or the treatment can be applied to the final products, e.g. the paint containing the polymer together with pigments fillers and additives such as are commonly used in paint formulations.

In the process of the invention any hydrolytic enzyme may be used which is capable of causing the decomposition of the ester monomer, especially an acrylate or methacrylate ester, to the corresponding acid. Particularly suitable classes of enzymes include esterases and lipases although amidases and proteases can be used. An especially suitable individual amidase enzyme for use in the process of the invention is that disclosed in our European Published Patent Application 0272025A which can be induced in strains of *Methylophilus methylotrophus* (formerly named *Pseudomonas methylotropha*), described in UK specification 1370892. Examples of suitable strains of *Methylophilus methylotrophus* include those deposited at the National Collections of Industrial and Marine Bacteria Ltd., 23 St. Machar Drive, Aberdeen, AB2 1RY. Scotland as strains NCIB 10508 to 10515 and 10592 to 10596 (particularly NCIB 10515).

Suitably the process of the invention is carried out at a temperature in the range 10° to 70° C., but not usually below ambient temperature, typically up to 50° C. preferably 30° to 50° C. and at a pH in the range 3 to 10, preferably 5 to 9. Preferably the enzyme is added to the medium containing the ester in an amount in the range 0.001 to 1% by weight (based on the weight of the medium).

Suitably the latex of the invention is an aqueous latex. Aqueous latexes suitable for coating compositions such as paints comprise homopolymers or more usually copolymers or ethylenically unsaturated carboxylic esters. In the copolymers other co-monomers include styrene, vinyl toluene, ethylene, propylene, butene-1 or copolymerised unsaturated carboxylic acids such as acrylic acid.

Further examples of suitable enzymes are listed below in Tables 1, 2 and 3. Table 1 lists enzymes which are generally suitable for use in the process of the invention to obtain marked reductions in levels of ethylenically unsaturated carboxylic esters. Table 2 lists preferred enzymes and Table 3 lists particularly prefered enzymes which for instance have been found to be capable of reducing the level of ester monomers present in their polymers to below 10 ppm. The lists are of examples only and are not exhaustive of the enzymes which may be used in the process of the invention.

In the lists the following abbreviations are used to indicate the different types of enzymes:

L: lipase or esterase
CE: acetylcholinesterase
P: protease
A: amidase
A(N): nitrilase
PL: phospholipase
AP: alkaline phosphatase

TABLE 1

| Enzyme | Source | Type |
| --- | --- | --- |
| 1. *Aspergillus niger* lipase | Biocatalysts Ltd | L |
| 2. *Chromobacterium viscoseem* lipase | Biocatalysts Ltd | L |
| 3. *Candida cylindracea* lipase | Biocatalysts Ltd | L |
| 4. *Mucor miehei* lipase | Biocatalysts Ltd | L |
| 5. *Pseudomonas fluorescens* lipase | Biocatalysts Ltd | L |
| 6. *Rhizopus niveus* lipase | Biocatalysts Ltd | L |
| 7. Pancreatic lipase | Biocatalysts Ltd | L |
| 8. Hog pancreas lipase | Fluka Chemicals Ltd | L |
| 9. Porcine pancreatic lipase | Sigma Chemical Company | L |
| 10. *Psuedomonas fluorescens* lipase | Sigma Chemical Company | L |
| 11. Porcine liver esterase | Sigma Chemical Company | L |
| 12. "LIPOLASE" lipase | Novo-Nordisk A/S | L |
| 13. Acetylcholinesterase type VI-S | Sigma Chemical Company | CE |
| 14. Subtilisin Carlsberg (type VIII) | Sigma Chemical Company | P |
| 15. Thermolysin (*Bacillus thermoproteolyticus*) | Diawa Kasei kk | P |
| 16. "ALCALASE" type DX (*Bacillus licheniformis*) | Novo-Nordisk A/S | P |
| 17. "ESPERASE" (*Bacillus* sp) | Novo-Nordisk A/S | P |
| 18. Amidase (*Methylophilus methylotrophus*) | ICI plc | A |
| 19. NOVO Sp 361 (Nitrilase) | Novo-Nordisk A/S | A(N) |
| 20. NOVOZYM" 244 Phospholipase A2 (bovine pancreas) | Novo-Nordisk A/S | PL |
| 21. Alkaline Phosphatase | Sigma Chemical Company | AP |
| 22. *Candida Cylindracea* LIP F5 | Enzymatix Ltd, Cambridge, UK | L |
| 23. *Mucor Miehei* LIP F7 | Enzymatix Ltd, Cambridge, UK | L |
| 24. *Pseudomonas Fluorescens* LIP B1 | Enzymatix Ltd, Cambridge, UK | L |
| 25. Porcine pancreatic Extract | Enzymatix Ltd, Cambridge, UK | L |
| 26. *Rhizopus* Sp LIP F1 | Enzymatix Ltd, Cambridge, UK | L |
| 27. *Rhizopus* Sp LIP F3 | Enzymatix Ltd, Cambridge, UK | L |
| 28. *Rhizopus* Sp LIP F4 | Enzymatix Ltd, Cambridge, UK | L |
| 29. *Rhizopus delemar* LIP F2 | Enzymatix Ltd, Cambridge, UK | L |
| 30. *Candida* Sp LIP F6 | Enzymatix Ltd, Cambridge, UK | L |
| 31. *Mucor* Sp LIP F8 | Enzymatix Ltd, Cambridge, UK | L |
| 32. *Aspergillus* Sp LIP F9 | Enzymatix Ltd, Cambridge, UK | L |
| 33. *Aspergillus Usamii* LIP F10 | Enzymatix Ltd, Cambridge, UK | L |
| 34. *Penicillium* SP LIP F11 | Enzymatix Ltd, Cambridge, UK | L |
| 35. *Penicillium* SP LIP F12 | Enzymatix Ltd, Cambridge, UK | L |
| 36. *Humicola lanuginosa* LIP F13 | Enzymatix Ltd, Cambridge, UK | L |
| 37. *Geotrichum candidum* LIP F14 | Enzymatix Ltd, Cambridge, UK | L |

TABLE 2

| Enzyme | Source | Type |
| --- | --- | --- |
| 4. *Mucor miehei* lipase | Biocatalysts Ltd | L |
| 5. *Pseudomonas fluorescens* lipase | Biocatalysts Ltd | L |
| 3. *Candida cylindracea* lipase | Biocatalysts Ltd | L |
| 6. *Rhizopus niveus* lipase | Biocatalysts Ltd | L |
| 7. Pancreatic lipase | Biocatalysts Ltd | L |
| 11. Porcine liver esterase | Sigma Chemical Company | L |
| 12. "LIPOLASE" lipase | Novo-Nordisk A/S | L |
| 14. Subtilisin Carlsberg (type VIII) | Sigma Chemical Company | P |
| 18. Amidase (*Methylophilus methylotrophus*) | ICI plc | A |
| 22. *Candida Cylindracea* LIP F5 | Enzymatix Ltd, Cambridge, UK | L |
| 20. NOVOZYM" 244 Phospholipase A2 (bovine pancreas) | Novo-Nordisk A/S | PL |

TABLE 3

| Enzyme | Source | Type |
| --- | --- | --- |
| 3. *Candida cylindracea* lipase | Biocatalysts Ltd | L |
| 5. *Pseudomonas fluorescens* lipase | Biocatalysts Ltd | L |
| 11. Porcine liver esterase | Sigma Chemical Company | L |
| 12. "LIPOLASE" lipase | Novo-Nordisk A/S | L |

Other enzymes useful in the process which may be mentioned include lipases derived from Rhizopus species such as *delemar, javanacius, Japonicus* and *oryzae;* Mucor species such as *avanicus;* Streptomyces species; Pseudomonas species such as *gladioli* and *cepacia; Humicola lanuginosa; Candida lipolytica* and various Penicillium species. In referring to enzymes as being obtained from particular sources, we mean that the specified sources represent the original genotype of the enzyme. Of course, using nucleic acid cloning techniques, enzymes can be expressed in species different from the source of the original genotype and enzymes expressed in a genotypically alien species are included as enzymes of the original genotypical source. For example, the commercially available enzyme 'Lipolase' from Novo-Nordisk A/S is stated to be genotypically lipase from *Humicola languinosa* but commercially manufactured using an Aspergillus expression vector for cloned DNA encoding for the enzyme.

The invention is illustrated by the following Examples:

EXAMPLE 1

Samples of acrylic latex containing 1000 ppm butyl acrylate or more were treated with pig liver esterase at 0.01% (w/w) or 0.1% (w/w) *Pseudomonas fluorescens* lipase. If necessary the pH of the latex was adjusted by the addition of 1.0M NaOH. The samples containing enzyme were mixed thoroughly and incubated at room temperature for 10 days. At intervals during the incubation, aliquots were removed and the levels of butyl acrylate and acrylic acid were determined by analysis.

FIG. 1 shows typical treatment profiles with the two enzymes for an acrylic latex at pH 6.0. The Figure shows graphs of butyl acrylate concentration (ppm) against incubation time (days) for the two enzymes. Controls performed at the same time showed no change in butyl acrylate concentrations over 10 days and no appearance of acrylic acid.

EXAMPLE 2

Samples of acrylic latex containing in excess of 1000 ppm butyl acrylate were adjusted to various pH values by the addition of 1.0M NaOH. Pig liver esterase was added to a final concentration of 0.01% (w/w) with thorough mixing. The latices were then incubated at room temperature and sampled at various time intervals for the determination of butyl acrylate and acrylic acid concentrations. Table 4 shows the effect of pH on the initial rate of butyl acrylate hydrolysis in acrylic latex by pig liver esterase compared to controls lacking enzyme.

TABLE 4

EFFECT OF pH ON THE HYDROLYSIS OF BUTYL ACRYLATE IN ACRYLATE LATEX BY PIG LIVER ESTERASE

| pH | Initial rate of butyl acrylate hydrolysis (ppm/day) |
|---|---|
| 5.4 | 210 |
| 6.0 | 590 |
| 7.0 | 780 |
| 8.0 | 920 |

EXAMPLE 3

Samples of commercial white matt emulsion paint containing between 1100–1700 ppm butyl acrylate were treated with the following enzymes (dose rate in % (w/w) in brackets): pig liver esterase (0.01) *Candida cylindracea* lipase (0.1), Novo Lipolase (0.1), *Methylophilus methylotrophus* amidase (0.1) and *Subtilisin carlsberg* (0.1). Incubations were carried out at room temperature except for Novo Lipolase and *Subtilisin carlsberg* which were at 30° C. After 3 days, samples were removed from the treated paint and analysed for butyl acrylate and acrylic acid concentration. Table 5 shows the reductions in butyl acrylate concentration achieved after 3 days treatment with enzyme. The most active enzyme reduced the butyl acrylate concentration to below 10 ppm in the paint.

TABLE 5

REDUCTIONS IN BUTYL ACRYLATE CONCENTRATIONS IN EMULSION PAINT BY TREATMENT WITH VARIOUS ENZYMES

| Enzyme | Amount of Butyl Acrylate Removed after 3 days (ppm) |
|---|---|
| Pig liver esterase | 1700 |
| *Candida cylindracea* lipase | 1040 |
| Novo lipolase | 830 |
| *Methylophilus methylotrophus* amidase | 370 |
| *Subtilisin carlsberg* | 258 |
| Control (enzyme) | 0 |

EXAMPLE 4

Aliquots of the white matt emulsion paint used in Example 3 were treated with *Methylphilus methylotrophus* amidase at 0.1% (w/w). After thorough mixing, samples were either incubated at room temperature or 50° C. At various time periods, aliquote were removed from the quantitation of butyl acrylate and acrylic acid levels. The initial rates of butyl acrylate hydrolysis observed were 129 ppm/day at room temperature and 364 ppm/day at 50° C. Thus a threefold increase in activity was seen at the higher temperature.

EXAMPLES 5 TO 7

De-odourisation of a latex:

Various amounts (as specified in Table 6) of the lipase derived from the yeast *Candida cylindracea* supplied by Sigma Chemical Company Limited of Poole, Dorset, England were added and stirred into a latex consisting of 50 wt % water and 50 wt % of a copolymer of butyl acrylate and methyl methacrylate. The latex contained 560 ppm of residual unpolymerised butyl acrylate monomer. The latex were maintained at 30° C. for 10 days during which time de-odourisation occurred by removal of a major proportion of the malodourous butyl acrylate monomer. After 10 days, 200 wt % of acetone was added to the latex to enable acrylate monomer remaining to be determined by high pressure liquid chromatography. The results obtained are shown in Table 6. The latex was found to have no odour of butyl acrylate when sniffed by an observer having a normal sense of smell.

TABLE 6

| Example | *Wt % lipase added | Amount Butyl Acrylate remaining at 10 days ppm |
|---|---|---|
| 5 | 0.1 | 19 |
| 6 | 0.05 | 31 |
| 7 | 0.025 | 33 |

*wt % is based on the weight of the latex.

EXAMPLES 8 TO 10

Effectiveness with various esters:

0.5 wt % (based on the weight of the sample) of the lipase used in Examples 5 to 7 was added to each of three 100 g of samples of de-ionised water containing 1000 ppm of one of three ethylenically unsaturated carboxylic ester monomers as specified in Table 7. The latex was maintained at 30° C. and shaken for 10 days. Then 200 g acetone was added to each sample to enable the amount of ester monomer remaining to be determined by gas/liquid phase chromatography. The results obtained are shown in Table 7. In all cases the amount of ester monomer remaining was below 100 ppm which was the lower limit of the sensitivity of the gas/liquid phase chromatography technique. The samples were found to have no odour of the esters which indicates that the concentration of ester was below 50 ppm.

TABLE 7

| Example | Ester Monomer | Amount remaining ppm |
|---|---|---|
| 8 | butyl acrylate | <100 |
| 9 | ethyl acrylate | <100 |
| 10 | methyl methacrylate | <100 |

EXAMPLES 11 TO 13

Effectiveness of supported lipase:

The procedure of Examples 8 to 10 was repeated except that the lipase used was obtained from the fungus *Mucor miehei*, was supported on a polystyrene support and was supplied by Novo Enzymes Limited of Fareham, Surrey, England under the trade name "LIPOZYME". The results obtained are shown in Table 9.

TABLE 9

| Example | Ester Monomer | Amount of Ester remaining after 10 days ppm |
|---|---|---|
| 11 | butyl acrylate | <100 |
| 12 | ethyl acrylate | <100 |
| 13 | methyl methacrylate | <100 |

In all cases, the samples showed no odour of the ester indicating that the concentration of ester was below 50 ppm.

EXAMPLE 14

Activity at higher temperature:

2.5 g of the supported lipase used in Examples 10 to 13 were added to 50 g of de-ionised water containing 1000 ppm of butyl acrylate. The water was maintained at 45° C. and stirred for two hours. Then 150 g acetone was added to the water (to enable the amount of butyl acrylate remaining to be determined by high pressure liquid chromatography) and the supported lipase was removed by filtration. The chromatography was performed and the concentration of butyl acrylate was found to be less than 500 ppm. The water was also found to have lost its odour of butyl acrylate.

The recovered supported lipase was re-used four times as above and was found not to have lost any of its activity.

EXAMPLE 15

Samples of a latex of a copolymer of methyl methacrylate and butylacrylate having a total solids content of about 52% of a type commercially used in and having a residual level of butyl acrylate monomer of 340 ppm were treated with the stated amounts (w/w) of following enzymes:

| | |
|---|---|
| *Methylophilus methylotrophua* amidase (ICI) | 0.625% |
| *Candida cylindricae* lipase (Biocatalysts) | 1.25% |
| *Mucor miehei* lipase (Biocatalysts) | 2.5% |
| Lipolase (Novo) | 2.5% |
| Pig liver esterase (Sigma) | 0.625% |
| *Pseudomonas fluorescens* lipase (Biocatalysts) | 2.5% |

Figure 2:
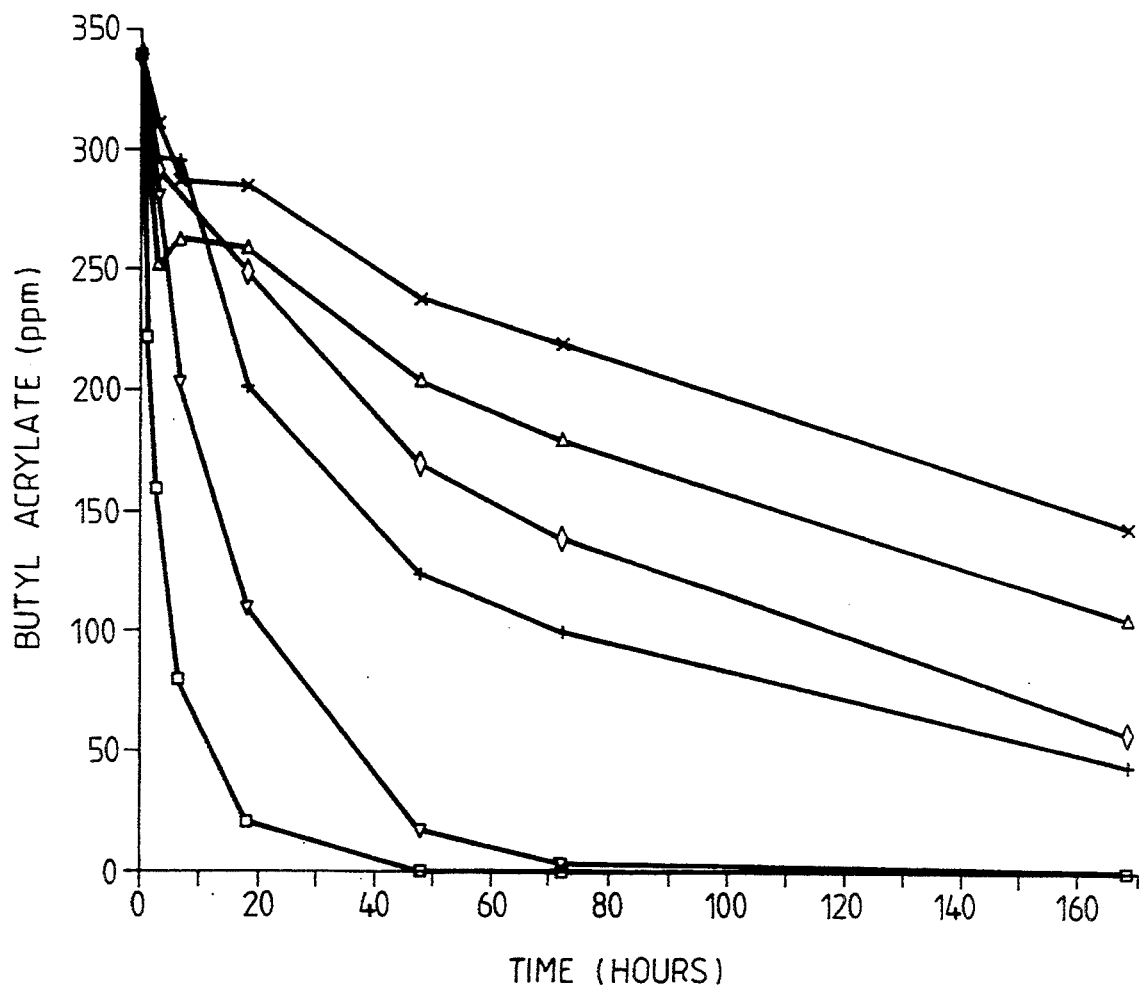

The latex samples containing the enzyme were incubated at 20° C. At suitable intervals, the levels of butyl monomer were determined by sampling, extraction and HPLC analysis. The results are set out in FIG. 2 which is a graph of measured butyl acrylate monomer lever against incubation time.

EXAMPLE 16

Samples of a latex of a copolymer of styrene, butyl acrylate and methacrylic acid and including a small proportion of α-methyl styrene and having a total solids content of about 40% commercially used in and having a residual level of butyl acrylate monomer of 790 ppm were treated with the stated amounts (w/w) of the following enzymes:

| | |
|---|---|
| *Candida cylindricae* lipase (Biocatalysts) | 1.25% |
| Lipolase (Nova) | 2.5% |
| *Mucor miehei* lipase (Biocatalysts) | 2.5% |
| *Pseudomonas fluorescens* lipase (Biocatalysts) | 2.5% |

The latex samples containing the enzyme were incubated at 20° C. At suitable intervals, the levels of buty acrylate monomer were determined by sampling, extraction and HPLC analysis. The results are set out in FIG. 3 which is a graph of measured butyl acrylate monomer level against incubation time.

We claim:

1. A method of removing residual amounts of an ethylenically unsaturated carboxylic acid ester monomer from a dispersion in a continuous liquid phase of particles of a polymer which contains residues derived from the ester monomer, which method comprises contacting the dispersion with a hydrolytic enzyme capable of decomposing the ester monomer in the presence of the stabilized dispersed polymer, under conditions suitable for the enzyme to decompose the ester.

2. A method as claimed in claim 1 wherein the ester monomer is an alkyl acrylate and/or methacrylate, the dispersion is an aqueous latex of the polymer and the enzyme is an esterase or lipase.

3. A method as claimed in either claim 1 or claim 2 wherein the hydrolytic enzyme is *Candida cylindracea* lipase, *Pseudomonas fluorescens* lipase, porcine liver esterase or "LIPOLASE" lipase.

4. A method as claimed in any one of claims 1 to 2 wherein the dispersion is contacted with the enzyme at a temperature of from ambient temperature of 50° C.

5. A method as claimed in any one of claims 1 to 2 wherein the dispersion is contacted with the enzyme at a pH of from 5 to 9.

6. A method as claimed in any one of claims 1 to 2 wherein the concentration of the ester monomer in the dispersion is at least 500 ppm prior to treatment with the enzyme.

* * * * *